United States Patent
Vardanyan et al.

(10) Patent No.: US 10,617,681 B2
(45) Date of Patent: *Apr. 14, 2020

(54) 1-ARYLALKYL-4-ACYLAMINOPIPERIDINE COMPOUNDS

(71) Applicant: ARIZONA BOARD OF REGENTS ON BEHALF OF THE UNIVERSITY OF ARIZONA, Tucson, AZ (US)

(72) Inventors: Ruben S. Vardanyan, Tucson, AZ (US); Victor J. Hruby, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/236,981

(22) Filed: Dec. 31, 2018

(65) Prior Publication Data

US 2019/0134018 A1 May 9, 2019

Related U.S. Application Data

(60) Division of application No. 15/709,394, filed on Sep. 19, 2017, now abandoned, which is a continuation-in-part of application No. 14/834,184, filed on Aug. 24, 2015, now Pat. No. 9,765,027.

(60) Provisional application No. 62/040,886, filed on Aug. 22, 2014.

(51) Int. Cl.
| | | |
|---|---|---|
| C07D 211/58 | (2006.01) | |
| C07D 405/12 | (2006.01) | |
| C07D 409/12 | (2006.01) | |
| A61K 31/4465 | (2006.01) | |
| A61K 31/451 | (2006.01) | |
| A61K 31/16 | (2006.01) | |

(52) U.S. Cl.
CPC .......... *A61K 31/4465* (2013.01); *A61K 31/16* (2013.01); *A61K 31/451* (2013.01); *C07D 211/58* (2013.01); *C07D 405/12* (2013.01); *C07D 409/12* (2013.01)

(58) Field of Classification Search
CPC ... C07D 211/58; C07D 405/12; C07D 409/12
See application file for complete search history.

(56) References Cited

U.S. PATENT DOCUMENTS

| 4,029,801 A | 6/1977 | Cavella et al. |
| 4,304,911 A | 12/1981 | Zenitz |
| 4,649,144 A | 3/1987 | Matsumoto et al. |
| 2004/0147503 A1 | 7/2004 | Zipfeil |

FOREIGN PATENT DOCUMENTS

| WO | WO 2007/028849 A1 | 3/2007 |
| WO | 2007058482 A1 | 5/2007 |
| WO | WO2012089738 A1 | 7/2012 |
| WO | WO2012149113 A1 | 11/2012 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Pubchem. Substance Record for SID 56006844. Deposit Date: Oct. 8, 2008. Retrieved on Nov. 11, 2015. Retrieved from the Internet. <URL: http://pubchem.ncbl.nlm.nlh.gov/substance/56006844#section=Top>. Entire document.
Pubchem. Substance Record for SID 150462038. Deposit Date: Oct. 23, 2012. [retrieved on Nov. 10, 2015]. Retrieved from the Internet. <URL: https://pubchem.ncbi.nlm.nih.gov/substance/150462038/version/1 >.entire document.
Invitation to Pay Additional Fees issued in application No. peT/US2015/046585, dated Nov. 2, 2015.
Boothby, L.A.,Doering, P.L., Buprenorphine for the treatment of opioid dependence, Am. J. Health-System Pharm., (2007), 64(3), 266-272.
Bosco, D.; Plastino, M.; Colica, C.; Bosco, F.; Arianna, S.; Vecchio, A.; Galati, F.; Cristiano, D.; Consoli, A.; Consoli, D., Opioid Antagonist Naltrexone for the Treatment of Pathological Gambling in Parkinson Disease, Clinical Neuropharmacology (2012), 35(3),118-120.
Brefel-Courbon, C.; Thaiamas, C.; Paul, H. P. S.; Senard, J-M.; iViontastruc, J-L.; Rascol, 0., a,2-Adrenoceptor antagonists. A new approach to Parkinson's disease? CNS Drugs (1998), 10(3), 1 89-207.

(Continued)

*Primary Examiner* — Shawquia Jackson
(74) *Attorney, Agent, or Firm* — Don D. Cha; HDC IP Law, LLP

(57) ABSTRACT

The present invention provides a compound of the formula:

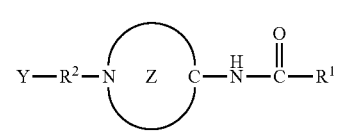

wherein
   ring Z is a 5-, 6- or 7-membered ring;
   $R^1$ is $C_{1-10}$ alkyl, $C_{1-10}$ haloalkyl, optionally substituted aralkyl, optionally substituted aryl, optionally substituted heteroaryl or optionally substituted heteroaralkyl;
   $R^2$ is $C_{1-10}$ alkylene; and
   Y is optionally substituted aryl, optionally substituted heteroaryl, or a moiety of the formula —C(=O)—$X^1$, wherein $X^1$ is —$OR^3$ or —$NR^4R^5$, where each of $R^3$, $R^4$ and $R^5$ is H or $C_{1-10}$ alkyl.

The present invention also provides a method for using compound of Formula I to treat a wide variety of clinical conditions.

17 Claims, No Drawings

(56) References Cited

OTHER PUBLICATIONS

Buck, K.; Ferger, B., The selective a,I adrenoceptor antagonist HEAT reduces L-DOPA-induced dyskinesia in a rat model of Parkinson's disease, Synapse (2010), 64(2), 117-126.

Capasso, A., D'Ursi, A., Pharmacological activity of new mu, k, delta receptor agonists and antagonists. Studies in Natur. Prod. Chem. (2005), 30, 797-823.

Comer, S. D., Sullivan, M. A,; Hulse, G. K., Sustained-release naltrexone: novel treatment for opioid dependence, Exp. Opin. Invest. Drugs, (2007), 16(8), 1285-1294.

Cunningham, C.W., Coop, A.,Therapeutic applications of opioid antagonists, Chimica Oggi, 24(3),54-57 (2006).

Eguchi, M., Recent advances in selective opioid receptor agonists and antagonists, Med. Res. Rev., (2004), 24(2),182-212.

Furst, S., Hosztafi, S., Friedmann, T., Structure-Activity Relationships of Synthetic and Semisynthetic Opioid Agonists and Antagonists, Curr. Med. Chern., (1995), 1, 423-40.

Goodman, A. J.; Le Bourdonnec, B.; Dolle, R. E. Mu opioid receptor antagonists: recent developments, ChemMedChem (2007), 2(11),1552-1570.

Heidbreder, C., Novel pharmacotherapeutic targets for the management of drug addiction, Eur. J. Pharmacol. (2005),526 (1-3), 101-112.

Hemy, B.; Brotchie, J. M., Potential of opioid antagonists in the treatment of levodopa-induced dyskinesias in Parkinson's disease (A review and discussion), Drugs & Aging (1996), 9(3), 149-158.

Hipkin, R. W.; Dolle, Roland E., Opioid receptor antagonists for gastrointestinal dysfunction, Ann. Rep. Med. Chem., (2010), 45, 143-] 55.

Husbands, S.M., Lewis, J.W., Opioid ligands having delayed long-term antagonist activity: Potential pharmacotherapies for opioid abuse, Mini-Revi. Med. Chern., (2003), 3(2),137-144.

Kaczor, A., Matosiuk, D., Non-peptide opioid receptor ligands—recent advances. Part II. Antagonists, Curr. Med. Chern., (2002), 9(17), 1591-1603.

Krishnan-Sarin, S., O'Malley, S.S., Opioid antagonists for the treatment of nicotine dependence, Med. Treat. Nicotine Depend., (2007) 123-135.

Lauretti, G.R., Highlights in opioid agonists and antagonists, Expert Rev. Neurotherapeut., 6(4), 613-622 (2006).

Leslie, J. B., Alvimopan: a peripherally acting Mu-. Opioid receptor antagonists, Drugs of Today (2007), 43(9),611-625.

Lewitt P. A; Hauser R. A; Lu M.; Nicholas A. P.; Weiner W.; Coppard N.; Leinonen M.; Savoia J.-M., Randomized clinical trial of fipamezole for dyskinesia in Parkinson disease (FJORD study), Neurology (2012),79(2),163-9.

Lowengrub, K., Iancu, I., Aizer, A., Kotler, M., Dannon, P.N., Pharmacotherapy of pathological gambling: review of new treatment modalities, Exp. Rev. Neurotherapeut., (2006), 6(12), 1845-1851.

Metcalf, M. D., Coop A., Kappa opioid antagonists: past successes and future prospects, The AAPS J., (2005), 7(3), E704-22.

Millan M. J., From the cell to the clinic: a comparative review of the partial D2/D3 receptor agonist and a2-adrenoreceptor antagonists, piribedil, in the treatment of Parkinson's disease Pharmacol. Therapeut. (2010), 128(2),229-73.

Portoghese, P. S., Bivalent ligands and the message-address concept in the design of selective opioid receptor antagonists, Trends Pharm. Sci., (1989), 10(6),230-5.

Portoghese, P. S., Selective nonpeptide opioid antagonists, Handbook of Experimental Pharmacology, (1993), 104/1 (Opioids I), 279-93.

Portoghese, P. S., The design of delta-selective opioid receptor antagonists, Farmaco, (1993), 48(2), 243-51.

Raisch, D.W., Fye, C. L., Boardman, K. D., Sather, M. R. Opioid dependence treatment, including buprenorphine/naloxone. Annals Pharmacother., (2002), 36(2),312-321.

Roozen, H. G., de Waart, R., van der Windt, D. A. W. M., van den Brink, W., de Jong, C. A. J., Kerkhof, A. J. F. M., A systematic review of the effectiveness ofnaltrexone in the maintenance treatment of opioid and alcohol dependence, Eur. Neuropsychopharmacol., (2006), 16(5),311-323.

Schmidhammer, H., Opioid receptor antagonists, Prog. Med. Chern., (1998), 35, 83-132.

Soyka, M.; Roesner, S., Opioid antagonists for pharmacological treatment of alcohol dependence—a critical review, Curf. Drug Abuse Rev., (2008), 1(3),280-291.

Stotts, A. L.; Dodrill, C. L.; Kosten, T. R. Opioid dependence treatment: options in pharmacotherapy, Exp. Opin. Pharmacother., (2009),10(11),1727-1740.

Takemori, A. E., Portoghese P S Selective naltrexone-derived opioid receptor antagonists, Ann. Rev. Pharm. Tox., (1992), 32, 239-69.

Taylor, R., Jr.; Pergolizzi, J. V., Jr.; Porreca, F.; Raffa, R. B. Opioid antagonists for pain Exp. Opin. Invest. Drugs, (2013), 22(4), 517-525.

Thayer, A., Drugs to Fight Addictions, Chem. Eng. News, (2006), 84(39), 21-44.

van Dorp, E. L. A., Yassen, A., Dahan, A., Naloxone treatment in opioid addiction: the risks and benefits, Exp. Opin. Drug Safety, (2007), 6(2), 125-132.

White, J.M., Lopatko, O.V., Opioid maintenance: a comparative review of pharmacological strategies, Expert Opin. Pharmacotherapy, (2007),8(1), 1-11.

Noods, J.H., Traynor, J.R., Evaluation of new compounds for opioid activity (2000), NIDA Research Monograph, Volume Date 2000, 181 (Problems of Drug Dependence 2000), (2001), 140-155.

Yuan, C.-S., Israel, R. J., Methylnaltrexone, a novel peripheral opioid receptor antagonist for the treatment of opioid side effects, Exp. Opin. Invest. Drugs, (2006), ] 5(5),541-552.

Zimmerman, D. M., Leander, J. D., Opioid antagonists: structure activity relationships, NIDA Research Monograph, (1990), 96, 50-60 (1990).

Office Action for U.S. Appl. No. 14/834,185, dated Apr. 28, 2016.
Office Action for U.S. Appl. No. 14/834,185, dated Aug. 25, 2016.
Office Action for U.S. Appl. No. 14/834,185, dated Mar. 31, 2017.
Archibald, J.L. et al., J. Med. Chem., 1974, 17(7), pp. 736-739.
Office Action of U.S. Appl. No. 15/709,394 dated May 17, 2018.
Office Action of U.S. Appl. No. 15/709,394 dated Oct. 2, 2018.

* cited by examiner

1-ARYLALKYL-4-ACYLAMINOPIPERIDINE COMPOUNDS

CROSS-REFERENCE TO RELATED APPLICATIONS

This application is divisional of U.S. patent application Ser. No. 15/709,394, filed Sep. 19, 2017, which is continuation-in-part of U.S. patent application Ser. No. 14/834,185, filed Aug. 24, 2015, which claims the priority benefit of U.S. Provisional Application No. 62/040,886, filed Aug. 22, 2014, all of which are incorporated herein by reference in its entirety.

STATEMENT REGARDING FEDERALLY FUNDED RESEARCH

This invention was made with government support under grant number R01 DK017420, R01 GM108040 and P01 DA006284 awarded by the National Institutes of Health. The government has certain rights in the invention.

FIELD OF THE INVENTION

The invention relates to novel pharmacological compounds, and more specifically to the creation of a new class of small molecules which simultaneously exhibit high binding affinities to the μ-, δ-, and κ-opioid receptors and the $\alpha_2$-adrenoreceptor. The binding activity is believed to be antagonistic at least with respect to the μ-opioid receptors. In addition to providing these compounds with novel pharmacological binding properties, the invention also describes detailed novel methods for the preparation of representative compounds and a scheme for the synthesis of related compounds that bind to the opioid receptors and/or $\alpha_2$-adrenoreceptor.

BACKGROUND OF THE INVENTION

Opioid antagonists are drugs which bind to the opioid receptors with higher affinity than opioid agonists but do not activate the opioid receptors. Commonly known opioid antagonists include drugs such as, for example, naltrexone, naloxone, nelmefene, nalorphine, and nalbuphine. Opioid antagonists effectively block the receptor from the action of both naturally occurring agonists (e.g., morphine, codeine, thebaine) and synthetic agonists (e.g., fentanyl, pethidine, levorphanol, methadone, tramadol, dextropropoxyphene) and uses include counteracting life-threatening depression of the central nervous and respiratory systems and thus are used for emergency overdose and dependence treatment (e.g., naloxone). There are many excellent reviews dedicated to different aspects of opioid antagonists [28-46].

Opioid receptor antagonists are known to modulate numerous central and peripheral effects including those associated with opioid abuse, the development of opioid tolerance and dependence, opioid-induced constipation, alcohol and cocaine abuse, depression, and immune responses. The diverse therapeutic applications of μ-opioid antagonists include opioid-overdose-induced respiratory depression, opioid and cocaine abuse, alcohol dependence, smoking cessation, obesity, psychosis and for the treatment of dyskinesia associated with Parkinson's disease.

The few opioid antagonists currently on the market are represented by very few drugs (e.g., naloxone, naltrexone, and nalorphine (a partial agonist)) that have been shown to have therapeutic utility in a variety of indications. During last two decades only Alvimopan—a peripherally acting μ-opioid antagonist for the treatment of postoperative ileus—has received approval as new drug. In addition, some azabicyclohexane derivatives and series of bi(hetero)aryl ethers as biological tools have been proposed as new chemical entities in this class of compounds.

Every chemical class of compounds with opioid-agonist activity has a structurally similar opioid-antagonist pair. Agonist-antagonist transformation in any of these cases takes place as a result of a small change in the structure of the agonist. The only exceptions, where the corresponding change for agonist-antagonist transformations has not been found, are the compounds of the fentanyl series.

Since the discovery of the "army" of opioid agonists of the fentanyl series (sufentanyl, alfentanyl, carfentanyl, remifentanyl, etc.) beginning in the 1960s, a structurally corresponding antagonist has not been found for any of these compounds. Thus, for decades there has been an evident gap in the art with respect to a possible specific structural change that could make possible the transformation of powerful opioid agonist properties of compounds of fentanyl series into powerful antagonists.

Similar to the general action of the opioid antagonists, antagonists of the adrenoreceptors (adrenergic receptors) bind to the adrenoreceptors and act to inhibit the action of those receptors. Alpha antagonists, or alpha-blockers, may selectively act at the $\alpha_1$-adrenoreceptors or at the $\beta_2$-adrenoreceptors, or they may non-selectively act at both receptors. Commonly known α-blockers include, for example, phenoxybenzamine and phentolamine (non-selective); alfuzosin and prazosin ($\alpha_1$-blockers); and atipamezole, idazoxan, mirtazapine and yohimbine ($\alpha_2$-blockers). Generally, α-blockers have shown to be effective in the treatment of various medical conditions, including Raynaud's disease, hypertension, scleroderma, anxiety and panic disorders, and in the treatment of dyskinesia associated with Parkinson's disease.

SUMMARY OF THE INVENTION

The present invention provides a compound of the formula:

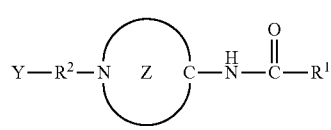

where
- ring Z is a 5-, 6- or 7-membered ring;
- $R^1$ is $C_{1-10}$ alkyl, $C_{1-10}$ haloalkyl, optionally substituted aralkyl, optionally substituted aryl, optionally substituted heteroaryl or optionally substituted heteroaralkyl;
- $R^2$ is $C_{1-10}$ alkylene; and
- Y is optionally substituted aryl, optionally substituted heteroaryl, or a moiety of the formula —C(=O)—$X^1$, wherein $X^1$ is —$OR^3$ or —$NR^4R^5$, where each of $R^3$, $R^4$ and $R^5$ is H or $C_{1-10}$ alkyl.

In some embodiments, compounds of the invention are of the formula:

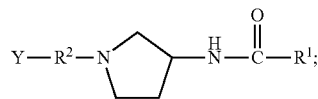

-continued

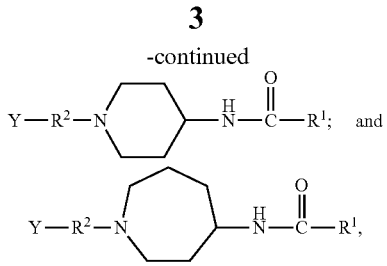

where R¹, R² and Y are those defined herein.

The present invention also provides a method for treating a subject suffering from a wide variety of clinical conditions by administering a therapeutically effective amount of a compound of the invention.

DETAILED DESCRIPTION OF THE INVENTION

Definitions

Unless the context requires otherwise, the following definitions are used.

"Alkyl" refers to a saturated linear monovalent hydrocarbon moiety or a saturated branched monovalent hydrocarbon moiety. Exemplary alkyl group include, but are not limited to, methyl, ethyl, n-propyl, 2-propyl, tert-butyl, pentyl, and the like.

"Alkylene" refers to a saturated linear saturated divalent hydrocarbon moiety or a branched saturated divalent hydrocarbon moiety. Exemplary alkylene groups include, but are not limited to, methylene, ethylene, propylene, butylene, iso-butylene, pentylene, and the like.

"Aryl" refers to a monovalent mono-, bi- or tricyclic aromatic hydrocarbon moiety of 6 to 15 ring atoms which is optionally substituted with one or more substituents. More specifically the term aryl includes, but is not limited to, phenyl, 1-naphthyl, and 2-naphthyl, and the derivatives thereof. When substituted, the aryl group typically contains one, two or three substituents within the ring structure. Moreover, when two or more substituents are present in an aryl group, each substituent is independently selected. Exemplary substituents for the aryl group include, but are not limited to, alkyl, haloalkyl, heteroalkyl, halo, nitro, cyano, optionally substituted phenyl, heteroaryl, haloalkoxy, —OR' (where R' is H, alkyl or a phenol protecting group) and carboxyl (i.e., a moiety of the formula —COX, where X is —OR$^a$ or —NR$^b$R$^c$, where each of R$^a$, R$^b$, R$^c$ is independently H, alkyl, or a corresponding protecting group.

"Aralkyl" refers to a moiety of the formula —R$^b$R$^c$ where R$^b$ is an alkylene group and R$^c$ is an optionally substituted aryl group as defined herein. Exemplary aralkyl groups include, but are not limited to, benzyl, phenylethyl, (halo-substituted phenyl)ethyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —CH$_2$Cl, —CF$_3$, —CH$_2$CF$_3$, —CH$_2$CCl$_3$, and the like.

The term "heteroaryl" means a monovalent monocyclic or bicyclic aromatic moiety of 5 to 12 ring atoms containing one, two, or three ring heteroatoms selected from N, O, or S, the remaining ring atoms being C. Exemplary heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like. The heteroaryl ring can optionally be substituted with one or more substituents, typically one or two substituents. When two or more substituents are present in heteroaryl, each substituent is independently selected. Exemplary substituents for heteroaryl include, but are not limited to, substituents described for aryl group above.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, oxalic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as narrower definitions, if any.

Compounds of the Invention:

One aspect of the invention provides compounds that can simultaneously bind with high affinity to opioid μ-, δ-, κ-receptors and also to α-adrenoreceptors, thereby exhibiting modulation-type interactions with those receptors. The interaction of the molecules with μ receptors is believed to have the character of antagonist action, based at least in part on the observed high affinity binding of the molecules with respect to the receptors.

Without being bound by any theory, it is believed that the principal structural change for agonist-antagonist transformation is the removal of a phenyl group from an N-phenyl-propionamide moiety of fentanyl as illustrated below, where N-(1-phenethylpiperidin-4-yl)-N-phenylpropionamide (A) is transformed to N-(1-phenethylpiperidin-4-yl)-N-propionamide (B). The present inventors have found that while compound (A) exhibits μ agonist property, compound (B), which lacks the phenyl moiety on the amide nitrogen, exhibits μ antagonist property in some instances with simultaneous modulation of delta-, kappa- and alpha-receptors:

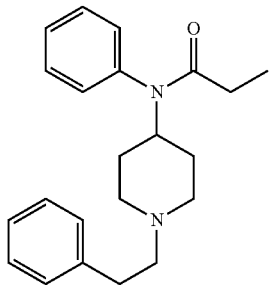

Fentanil (A)

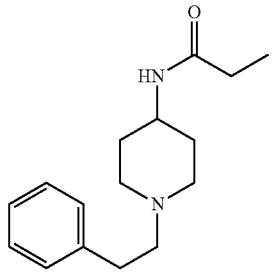

μ-opioid antagonist (B)

Accordingly, some aspects of the invention provide N-substituted piperidin-4-yl compounds of Formula I:

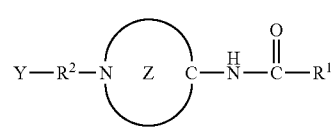

I where the phenyl group on the amide nitrogen of has been replaced with hydrogen. With regards to Compound of Formula I, in some embodiments Z is a 5-, 6- or 7-membered ring, typically unsubstituted; $R^1$ is $C_{1-10}$ alkyl, $C_{1-10}$ haloalkyl, optionally substituted aralkyl, optionally substituted aryl, optionally substituted heteroaryl or optionally substituted heteroaralkyl; $R^2$ is $C_{1-10}$ alkylene; Y is optionally substituted aryl, optionally substituted heteroaryl, or a moiety of the formula —C(=O)—$X^1$, wherein $X^1$ is —$OR^3$ or —$NR^4R^5$, where each of $R^3$, $R^4$ and $R^5$ is H or $C_{1-10}$ alkyl. In some aspects of the invention, when $R^1$ is optionally substituted aryl, then Y is a substituted heteroaryl, or a moiety of the formula —C(=O)—$X^1$. Still in another aspect of the invention, when Y is heteroaryl or aryl, then $R^1$ is $C_{1-10}$ alkyl, $C_{1-10}$ haloalkyl, or optionally substituted heteroaryl.

In some embodiments, compounds of the invention include compounds of the formulas:

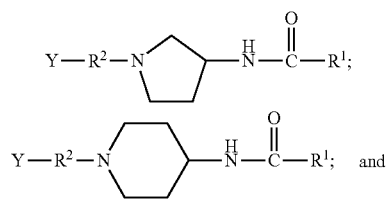

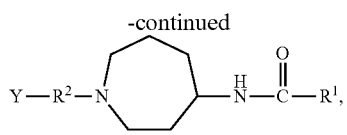

where R¹, R² and Y are those defined herein.

Yet still in another aspect of the invention, compounds of invention are those of Formula I as broadly disclosed above provided when Y is heteroaryl, R¹ is not optionally substituted phenyl, in particular R¹ is not phenyl.

Still in another aspect of the invention, compounds of invention are those of Formula I as broadly disclosed above provided when Y is phenyl, R¹ is not substituted phenyl.

In some embodiments, R¹ is selected from the group consisting of $C_{1-8}$ alkyl, $C_{1-8}$ haloalkyl, optionally substituted phenyl, and optionally substituted furyl. In some instances, R1 is selected from the group consisting of ethyl, 7-bromoheptyl, fur-2-yl, fur-3-yl, and phenyl.

Yet in other embodiments, R² is $C_{1-4}$ alkylene. In one particular embodiment, R² is ethylene.

Still in other embodiments, Y is selected from the group consisting of optionally substituted phenyl, optionally substituted furyl, optionally substituted thiophenyl and a moiety of the formula —C(=O)—X¹, where X¹ is those defined herein. Within these embodiments, in some instances Y is selected from the group consisting of phenyl, thiophenyl (typically thiophen-2-yl), and a moiety of the formula —C(=O)—OR³, where R³ is $C_{1-10}$ alkyl.

Still further, combinations of the various embodiments of different variables described herein form other embodiments. For example, in one particularly preferred embodiment R¹ is ethyl, R² is ethylene, Y is phenyl. In this manner, a variety of specific compounds are embodied within the present invention including, but not limited to, N-(1-phenethylpiperidin-4-yl)propionamide ("HCV-3"), methyl 3-(4-propionamidopiperidin-1-yl)propanoate, N-(1-phenethylpiperidin-4-yl)furan-2-carboxamide, N-(1-phenethylpiperidin-4-yl)furan-3-carboxamide, N-(1-(2-(thiophen-2-yl)ethyl)piperidin-4-yl)propionamide, 8-bromo-N-(1-phenethylpiperidin-4-yl)octanamide, and N-(1-phenethylpiperidin-4-yl)benzamide.

Synthesis:

Compound of the invention can be readily prepared by one skilled in the art having read the present disclosure. It should be appreciated that although the following schemes for producing compounds of Formula I often indicate exact structures, methods of the present invention apply widely to analogous compounds of Formula I, given an appropriate consideration to protection and deprotection of reactive functional groups by methods standard to the art of organic chemistry. For example, hydroxyl groups, in order to prevent unwanted side reactions, sometimes need to be converted to ethers or esters during chemical reactions at other sites in the molecule. The hydroxyl protecting group is then removed to provide the free hydroxyl group. Similarly, amino groups and carboxylic acid groups can be derivatized to protect them against unwanted side reactions. Typical protecting groups, and methods for attaching and cleaving them, are described fully in the above incorporated references by T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 (John Wiley and Sons, 1971-1996).

One particular method of producing compounds of the invention is illustrated in Scheme I below:

Scheme I

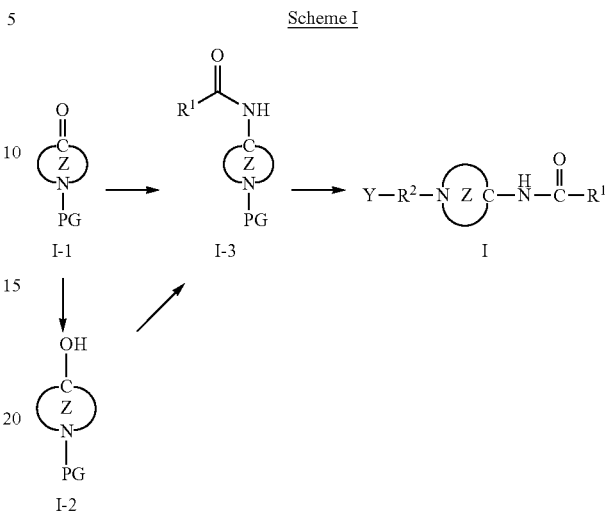

PG = Protecting Group;
R¹ = methyl, ethyl, isopropyl, butyl, octyl, 7-bromoheptyl, fur-2-yl, methoxyfur-2-yl, chloro fur-2-yl, fur-3-yl, methoxy fur-2-yl, chlorofur-3-yl, phenyl, methoxyphenyl, trimethylfluorophenyl, fluorophenyl, etc.;
R² = methylene, ethylene, propylene, butylene, octylene, etc.
Y = phenyl, methoxyphenyl, trifluoromethylphenyl, chlorophenyl, fluorophenyl, thiophen-2-yl, methoxythiophen-2-yl, chlorothiophen-2-yl, fluorothiophen-2-yl, thiophen-3-yl, methoxythiophen-3-yl, chlorothiophen-3-yl, fluorothiophen-3-yl, fur-2-yl, methoxyfur-2-yl, chlorofur-2-yl, fur-3-yl, methoxy fur-2-yl, chloro fur-3-yl, phenyl, methoxyphenyl, trimethylfluorophenyl, fluorophenyl, etc.;

Briefly, compound I-1 is reduced to alcohol, via Reformatsky reaction or a simple reduction using, for example, a reducing agent such as $NaBH_4$, $NaB(CN)H_3$, $LiAlH_4$, etc. Compound I-2 is then subject to a Ritter type reaction (using R¹—CN compound in the presence of a strong base, such as sulfuric acid) to produce compound I-3. Alternatively, compound I-2 can be subjected to a substitution reaction (e.g., an $S_N1$ or $S_N2$-type reaction by converting the hydroxyl group into a leaving group and displacing with an amine group. The amine group can then be acylated to produce compound I-3. A wide variety of acylating agent can be used to acylate the amine compound. Exemplary acylating agents include, acetic anhydride, acetyl chloride, butyric anhydride, 2-furoyl chloride, methoxy 2-furoyl chloride, chloro 2-furoyl chloride, fluoro 2-furoyl chloride, 3-furoyl chloride, methoxy 3-furoyl chloride, chloro 3-furoyl chloride, fluoro 3-furoyl chloride, 2-thiophenoyl chloride, methoxy 2-thiophenoyl chloride, chloro 3-thiophenoyl chloride, 3-thiophenoyl chloride, methoxy 3-thiophenoyl chloride, chloro 3-thiophenoyl chloride, fluoro 3-thiophenoyl chloride, benzoyl chloride, methoxy benzoyl chloride, chloro benzoyl chloride, fluoro benzoyl chloride, trifluoromethyl benzoyl chloride, as well as Cl—C(=O)—$(CH_2)$n-Ar, where n is 1-10 and Ar is optionally substituted phenyl, including but not limited to, phenyl, methoxy phenyl, chlorophenyl, trifluoromethylphenyl, etc.

Compound I-3 is deprotected to remove the protection group (PG) and alkylated to yield compound of Formula I. A wide variety of alkylating agents can be used to introduce the moiety "—R²—Y". such alkylating agents include a compound of the formula X—R²—Y, where X is a leaving group and $R^2$ and Y are those defined herein. Suitable leaving groups include halides, such as bromide, chloride, or iodide, mesylates (e.g., methanesulfonate), tosylate, etc.

It should also be apparent to those skilled in the art that the reaction need not be carried out in the sequence outlined in Scheme I. For example, "—$R^2$—Y" group can be introduced prior to introducing "$R^1$—C(=O)—NH—" moiety to compound I-1. Thus, the compounds of the invention can be prepared by a variety of methods.

Utility:

The compounds of the invention have a variety of physiological properties. In particular, the present inventors have discovered that compounds of the invention can modulate a variety of receptors including, but not limited to, $\mu$-, $\delta$-, and $\kappa$-opioid receptors and $\alpha_2$-adrenoreceptor, in particular $\alpha_{2B}$-adrenoreceptor. In particular, the compounds of the invention are found to be antagonists of these receptors. Accordingly, any clinical conditions that are due or associated with at least in part to abnormal activation of one or more of these receptors can be treated by the compounds of the invention.

In some embodiments, compounds of the invention are found to be opioid antagonists. As such, compounds of the invention bind to the opioid receptors with higher affinity than opioid agonists but do not activate the opioid receptors. Thus, compounds of the invention can be used to effectively block the receptor from the action of both naturally occurring opioid agonists (e.g., morphine, codeine, thebaine) and synthetic opioid agonists (e.g., fentanyl, pethidine, levorphanol, methadone, tramadol, dextropropoxyphene). Accordingly, compounds of the invention can be used in a variety of clinical conditions associated with opioid use including, but not limited to, counteracting life-threatening depression of the central nervous and respiratory systems. Therefore, compounds of the invention can be used for emergency overdose and dependence treatment.

Compounds of the invention can modulate numerous central and peripheral effects including those associated with opioid abuse, the development of opioid tolerance and dependence, opioid-induced constipation, alcohol and cocaine abuse, depression, and immune responses. The diverse therapeutic applications of compounds of the invention include opioid-overdose-induced respiratory depression, opioid and cocaine abuse, alcohol dependence, smoking cessation, obesity, psychosis and for the treatment of dyskinesia associated with Parkinson's disease.

In another aspect of the invention, the present inventors have discovered that compounds of the invention are antagonists of adrenoreceptors. Thus, compounds of the invention bind to the adrenoreceptors and inhibit the action of these receptors. $\alpha$-Adrenoreceptor antagonists (commonly known as $\alpha$-blockers) may selectively bind to the $\alpha_1$-adrenoreceptors or the $\alpha_2$-adrenoreceptors, or they may bind nonselectively to both adrenoreceptor types. In some embodiments, compounds of the invention are found to be selective $\alpha_{2B}$-adrenoreceptor antagonists. As used herein, the term "selective $\alpha_{2B}$-adrenoreceptor antagonist" means that the ratio of binding to $\alpha_{2B}$-adrenoreceptor compared to other adrenoreceptor is at great than 1:1, typically, at least about 1.5:1, often at least about 2:1, more often at least about 5:1, and most often at least about 10:1. Compounds of the invention can be used to treat various clinical conditions that are related to or associated with abnormal activation of adrenoreceptors including, but not limited to, Raynaud's disease, hypertension, scleroderma, anxiety and panic disorders, and in the treatment of dyskinesia associated with Parkinson's disease.

Utility for compounds of various receptor antagonists are known. See, for example, Singleton et al., *Cancer,* 2015, 121(16), 2681-2688 (use of $\mu$-opioid receptor antagonists in cancer treatment); Jackson et al., *Neuropharmacology,* 2015, 97, 270-274 (use of $\kappa$-opioid receptor antagonist for nicotine withdrawal); Bear et al., U.S. Pat. Appl. Publication No. US 20150202199 A1 (treatments for depression and other diseases using dopaminergic agents); Noble et al., *British Journal of Pharmacology,* 2015, 172(16), 3964-3979 (opioid receptor antagonists for drug abuse and/or the prevention of relapse treatment); Brokjaer et al., *Neurogastroenterology & Motility,* 2015, 27(5), 693-704 (opioid antagonists for treatment of gastrointestinal side effects such as pain); Labuzek et al., *Pharmacological Reports,* 2014, 66(5), 811-820 (opioid antagonists for pharmacotherapy for gambling disorder); Soyka et al., *Current Drug Abuse Reviews,* 2008, 1(3), 280-291 (opioid antagonists for pharmacological treatment of alcohol dependence); Nutt et al., *Psychopharmacology,* (London, United Kingdom), 2014, 28(1), 8-22 (treatment of alcohol dependence); Tek et al., *Journal of Clinical Psychopharmacology,* 2014, 34(5), 608-612 (use of opioid antagonists in arresting antipsychotic-associated weight gain); Shi et al., *Guoji Yaoxue Yanjiu Zazhi,* 2013, 40(4), 439-442 (combinations of opioid agonists and opioid antagonists to treat side effects of opioid agonists and decrease risk of drug abuse); Wang et al., *Expert Opinion on Investigational Drugs,* 2013, 22(10), 1225-1227 (use of opioid antagonists for treatment of opioid-induced constipation); Taylor et al., *Expert Opinion on Investigational Drugs,* 2013, 22(4), 517-525 (use of opioid antagonists as analgesics); Zagon et al., PCT patent application publication number WO 2013016480 A1 (use of opioid antagonists for treatment of epithelial wounds); Pisak et al., PCT Patent Application Publication No. WO 2012134410 A1 (use of opioid antagonists for treating scleroderma including systemic sclerosis); Hopp et al., PCT Patent Application Publication No. WO 2012089738 A1 (use of a combination of opioid agonists and opioid antagonists for the treatment of Parkinson's disease and associated symptoms); Tenhola et al., *J. Endocrinological Investigation,* 2012, 35(2), 227-230 (effect of opioid antagonists on sex hormone secretion, e.g., using an opioid antagonists to increase the secretion of GnRH in the hypothalamus which then causes a pulsatile release of LH in the pituitary and secretion of testosterone); Miller et al., *Amer. J. Health-System Pharmacy,* 2011, 68(15), 1419-1425 (use of opioid antagonists for management of opioid-induced pruritus); Toledano et al., U.S. Pat. Appl. Publ. No. 20110269727 A1 (using opioid antagonists and direct-acting $\alpha_2$-adrenergic agonists to reduce allodynic back pain); Pisak et al., PCT Patent Application Publication No. WO 2011123084 A1 (using an opioid receptor antagonist to treat herpes zoster disease); Ockert et al., *J. Addiction Med.,* 2011, 5(2), 110-114 (using an opioid antagonist for outpatient opioid detoxification and/or the treatment of opioid withdrawal); Moss et al., U.S. Pat. Appl. Publ. No. 20100286059 A1 (use of opioid antagonists for inhibiting or reducing, cellular proliferation and migration, such as endothelial cell proliferation and migration, including that associated with angiogenesis, as well as attenuating cancerous tumor growth and metastasis); Zagon et al., U.S. Pat. Appl. Publ. No. US 20100273821 A1 (using opioid antagonists to treat dry eye); Lobmaier et al., *Eur. J. Clin. Pharm.,* 2010, 66(6), 537-545 (use of the opioid antagonists for the treatment of intoxication and overdose); Stotts et al., *Expert Opinion on Pharmacotherapy,* 2009, 10(11), 1727-1740 (using opioid antagonists for treating opioid dependency); Hopp et al., PCT Patent Application Publication No. WO 2010003963 A1 (using opioid antagonists for treating urinary retention); and Hayward et al., PCT Patent Application Publication No. WO 2009156889 A1 (using opioid antagonists for treating obesity, obesity-related co-morbidities, and CNS disorders). Accordingly, compounds of the invention can be used treat all of these clinical conditions. In addition, compounds of the invention can be used in the treatment of various forms of depression and/or mood disorders, including, for example, breakthrough depression and treatment-refractory depression, and other mood disorders.

Some of the more specific exemplary clinical conditions that can be treated by compounds of the invention include, but are not limited to, hemorrhagic shock, nicotine withdrawal symptoms, gastrointestinal side effects of opioids, cancer therapy, epithelial wounds, herpes zoster infection, and opioid-induced pruritus.

Administration and Pharmaceutical Composition:

The present invention includes pharmaceutical compositions comprising at least one compound of the invention or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula I, as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula I or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula I and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula I, or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

1-Phenethylpiperidin-4-one Oxime (Compound V)

1-Phenethylpiperidin-4-one (10.15 g (0.05 mol) dissolved in 60 mL of ethanol) was added drop-wise at 0° C. to a solution of hydroxylamine in water. The water solution of hydroxylamine was preliminarily prepared by adding at 0° C. in portions 13.8 g (0.1 mol) of $K_2CO_3$ to the solution of 6.95 g (0.1 mol) hydroxylamine hydrochloride in 50 mL of water. The mixture was set aside for a night. Ethanol was evaporated under slight vacuum. Water (~100 mL) was added, and the mixture was stirred on ice bath for an hour. The separated solid product was filtered, washed with water and allowed to air-dry. The crude oxime (10.71 g (98.25%), m.p. 132-134° C.) was reserved for use in the next reaction without further purification. Analysis with electrospray ionization mass spectrometry (MS (ESI)) resulted in a peak at 219.1 (MH+).

1-Phenethylpiperidin-4-amine (Compound VI)

1-Phenethylpiperidin-4-one oxime (6.54 g (0.03 mol)) was dissolved in 100 mL of dry i-AmOH on heating. A ten-fold excess of sodium (6.9 g (0.3 mol)) was slowly (1 hour) added to the stirred solution in small pieces, while the temperature was maintained around 110°. The solution was stirred on heating at 110° for two hours and left to cool to room temperature. 150 mL of ether, followed by 75 mL of water, was then added to the solution. The organic layer was separated and dried on $MgSO_4$. After evaporation of solvents under slight vacuum, the product was distilled to give 4.3 g (70%) of 1-phenethylpiperidin-4-amine (VI) with a boiling point of 138-142°/1.5 mm. MS (ESI): 205.0 (MH+).

N-(1-Phenethylpiperidin-4-yl)propionamide (Compound I)

Propionyl chloride (2.775 g (0.03 mol)) in 5.55 mL of $CHCl_3$ was added drop-wise on stirring to the cooled (0° C.) solution of 4.08 g (0.02 mol) 1-phenethylpiperidin-4-amine and 3.03 g (0.03 mol) of $Et_3N$ in 30 mL of $CHCl_3$. The mixture was left to come to room temperature and stirred overnight. After working up with 5% solution of $NaHCO_3$ (2.52 g (0.03 mol)) in 47.88 $H_2O$, the organic layer was separated, washed with water and dried on $MgSO_4$. After evaporation of solvents under slight vacuum, the residue was crystallized from hexane to give 4.9 g (94%) of N-(1-phenethylpiperidin-4-yl)propionamide (I) with m.p. 134-135°. MS (ESI): 261.2 (MH+). $^1$H NMR (600 MHz, $CDCl_3$): δ 7.27 (t, J=7.4 Hz, 2H), 7.19 (m, 3H), 5.32 (d, J=7.4 Hz, 1H), 3.82 (qt, J=7.8, 4.2 Hz, 1H), 2.92 (dt, J=11.8, 3.4 Hz, 2H), 2.79 (m*, 2H), 2.59 (m*, 2H), 2.19 (q, J=7.5 Hz, 2H), 2.18 (m, 2H), 1.95 (dtd, J=12.4, 4.4, 1.7 Hz, 2H), 1.46 (qd, J=11.7, 3.8 Hz, 2H), 1.15 (t, J=7.5 Hz, 3H). $^{13}$C NMR (150 MHz, $CDCl_3$): δ 173.0, 140.2, 128.6, 128.4, 126.0, 60.4, 52.3, 46.3, 33.7, 32.3, 29.8, 9.9.

N-(1-Phenethylpiperidin-4-yl)propionamide Oxalate (Compound VII)

Oxalic acid (1 g (0.011 mol)) in 10 mL of ethanol was added drop-wise to the solution of 2.93 g (0.011 mol) of N-(1-phenethylpiperidin-4-yl)propionamide (I) in 29.3 mL of ethanol. The mixture was set aside overnight. The obtained crystals were then separated and dried in a desiccator over $P_2O_5$ to give 3.5 g of N-(1-phenethylpiperidin-4-yl)propionamide oxalate (VII) with m.p. 216-218 (MS (ESI): 261.2 ([M+H]).

The compound designated as HCV-3 was then subject to cellular functional assay and results reported below:

Cellular Functional Assays

| Experimental Assay | Catalog Ref Client Com Batch | Compound Test Conce % of Contro % of Agonist Response | $1^{st}$ | $2^{nd}$ | Mean | Reference $EC_{50}$ Ref(M) |
|---|---|---|---|---|---|---|
| 27/07/201 α 2B(h1813 | HCV-3 1 | 1000233221.0E−05 | 7.1 | 9.2 | 5.1 | 7.1 dexmedetc 1.3E−08 |
| 27/07/201 κ (KO 2071 | HCV-3 1 | 1000233221.0E−05 | −4.2 | −10.3 | 1.8 | −4.2 U 50488 1.6E−09 |
| 27/07/201 μ (MOP) 1392 | HCV-3 1 | 1000233221.0E−05 | 33.5 | 28.1 | 38.9 | 33.5 DAMGO 4.2E−09 |

Cellular Functional Assays

| Experimental Assay | Catalog Ref Client Com Batch | Compound Test Conce % Inhibition Agonist Response (% of Control) | $1^{st}$ | $2^{nd}$ | Mean | Reference IC50Ref(N KbRef(M) |
|---|---|---|---|---|---|---|
| 27/07/201 α2B(h1814 | HCV-3 1 | 1000233221.0E−05 −28 | 116.8 | 138.7 | 127.8 | yohimine 3.7E−07 4.8E−08 |
| 27/07/201 κ (KO 2072 | HCV-3 1 | 1000233221.0E−05 6 | 112.4 | 76.5 | 94.4 | nor-BNI 4.3E−10 7.2E−11 |
| 27/07/201 μ (MOP) 1393 | HCV-3 1 | 1000233221.0E−05 −1 | 100.1 | 101.8 | 101.0 | CTOP 2.1E−07 2.3E−08 |

Compound HCV-3 also was tested for hERG inhibition. Over the concentration range tested (up to 25 micromolar) no dose-response was obtained. Therefore the inhibition $IC_{50}$ was considered as >25 micromolar. There was a hint of some inhibition at the top concentration of 25 micromolar, with 32.5% inhibition observed (insufficient to generate an $IC_{50}$ value). As such, this compound is categorised as having weak or no hERG inhibition. The control compounds behaved as expected in the assay.

Compound HCV-3 also was tested for CYP inhibition, and was found to inhibit CYP2D6, and to weakly inhibit CYP2C19. However, with CYP2C19 the inhibition was too weak to generate an $IC_{50}$ value, and we observed just 36.4% inhibition at the top concentration of 25 micromolar. With CYP2D6, an $IC_{50}$ of 4.2 micromolar was observed. Thus, this compound was considered to be a moderate CYP2D6 inhibitor, and a weak CYP2C19 inhibitor. No inhibition was observed at CYP2B6, CYP2C9, CYP3A4 (with either substrate), CYP2C8 or CYP1A2. The significance of this CYP2D6 inhibition will depend on the levels of the compound in vivo. Compound HCV-3 also was tested in cellular and nuclear receptor functional assays and was also subjected to AMES testing.

Compound HCV-3 was negative for genotoxicity against both strains used in this assay (TA98 and TA 100) up to a maximum tested concentration of 1 mg/mL, in both the absence and presence of S9 metabolic activation. The assay controls behaved as expected.

Compound HCV-3 also was subjected to in vitro metabolic disposition in mouse, rat, monkey and human microsomes. The test compound was incubated with pooled liver microsomes, since drip stability in liver microsomes can be predictive of drug stability in vivo. Aliquots were taken at 0, 5, 15, 30 and 45 minutes and quenched immediately. The samples were extracted and analyzed by LC-MS/MS. Compound HCV-3 was observed to have low clearance in human, monkey and mouse microsomes, and moderate clearance in rat.

Compound HCV-3 also was subjected to MDCK permeability assay. The compound was observed to be highly permeable in the MDCK assay. There was a slight difference between the plus and minus inhibitor data in terms of the efflux ratio obtained (1.48 minus inhibitor, versus 0.929 plus inhibitor). A ratio of greater than 2 generally indicates that efflux, i.e., blood brain barrier permeability, is occurring. The control compounds behaved as expected, with prazosin (a P-gp substrate) showing efflux in the absence of Cyclosporin A, which was inhibited in its presence.

Various derivatives of the above compounds with potential opiod and alpha antagonist activity were prepared using Scheme I as well as procedures describe herein.

Synthesis of 1-benzylpiperidin-4-one Oxime 28.35 g (1 equiv., 0.15 mol) of 1-benzylpiperidin-4-one was dissolved in 60 mL of EtOH and then cooled to 0° C. using an ice bath. A solution containing 20.85 g (2 equiv., 0.30 mol) of hydroxylamine hydrochloride dissolved in 75 mL of $H_2O$ was prepared and then added dropwise to the reaction mixture followed by dropwise addition of a solution containing 20.7 g (1 equiv., 0.15 mol) of $K_2CO_3$ dissolved in 75 mL of $H_2O$. The reaction mixture was then brought to room temperature and stirred overnight. The EtOH was then removed via rotary evaporation and the reaction mixture was then cooled in an ice bath to allow the product to crystallize out of solution. The product was filtered and washed several times with $H_2O$ and recrystallized in EtOH. Yield: 27.78 g (70.17%).

Synthesis of 1-benzylpiperidin-4-amine

A solution containing 6.12 g (1 equiv., 0.03 mol) of 1-benzylpiperidin-4-one oxime dissolved in 90 mL of iso-amyl alcohol was prepared and heated to approximately 110° C. 6.9 g (10 equiv., 0.3 mol) of Na metal was then added slowly to the reaction mixture. After addition of Na, the reaction mixture was allowed to cool to room temperature and stirred until the reaction mixture turned into a thick slurry. The slurry was dissolved in 50 mL of ethyl acetate and 25 mL of $H_2O$. The organic layer was separated and washed with $H_2O$ (2×20 mL) followed by drying over anhydrous magnesium sulfate. The solvent was removed via rotary evaporation, resulting in a yellow oil. The crude product was purified via column chromatography utilizing silica gel and a DCM:MeOH solvent system in a ratio of 4:1 with an additional 1% of $Et_3N$. Yield: 3.7 g (64%).

Synthesis of N-(1-benzylpiperidin-4-yl)propionamide

A solution of 3.7 g of 1-benzylpiperidin-4-amine (1 equiv., 0.019 mol) dissolved in 45 mL of dry dichloromethane was prepared followed by the addition of 5 mL of $Et_3N$ (2.6 equiv., 0.05 mol). The reaction mixture was then cooled to 0° C. using an ice bath, and then 2.17 mL (1.3 equiv., 0.025 mol) of propionyl chloride dissolved in 10 mL of dry dichloromethane was added dropwise to the reaction mixture. The reaction mixture was then warmed to room temperature and stirred overnight. Once the reaction was complete, 4 mL of $NH_4OH$ and 45 mL of $H_2O$ were added to the reaction mixture. The organic layer was separated, and the aqueous layer was washed with dichloromethane (3×20 mL) followed by $NaHCO_3$ solution and brine. The organic extracts were dried over anhydrous magnesium sulfate and the solvent was removed via rotary evaporation, resulting in a white solid. The product was washed with hexanes to obtain an analytically pure sample. Yield: 2.8 g (72%).

Synthesis of N-(piperidin-4-yl)propionamide

About 0.7 g of N-(1-benzylpiperidin-4-yl)propionamide (1 equivalent, 0.003 moles) were added to a parr hydrogenation flask and dissolved in 30 mL of EtOH. The solution was then degassed with argon for 30 min followed by the addition of 0.07 g of 10% Pd/C (0.2 equiv., $6.58 \times 10^{-4}$ mol) and 0.07 g of 20% $Pd(OH)_2$ (0.17 equiv., $4.98 \times 10^{-4}$ mol). The black solution was then degassed with argon for an additional 15 min. The reaction mixture was then charged with 50 psi of $H_2$ gas and shaken for 24 h. The product was filtered through Celite and the solvent was removed via rotary evaporation. No further purification was required. Yield: 0.467 g (99%).

Synthesis of methyl 3-(4-propionamidopiperidin-1-yl)propanoate (CRA5)

About 0.1 g of N-(piperidin-4-yl)propionamide (1 equiv., $5.26 \times 10^{-4}$ moles) was dissolved in 2 mL of dry acetonitrile followed by the addition of 0.071 mL of methyl acrylate (1.5 equiv., $7.89 \times 10^{-4}$ mol). The reaction mixture was refluxed overnight. The solvent was removed via rotary evaporation.

The crude product was purified by washing with hexanes followed by drying under high vacuum. Yield: 0.90 g (71%).

Synthesis of N-(1-(2-(thiophen-2-yl)ethyl)piperidin-4-yl)propionamide (CRAS1)

About 0.1 g of N-(piperidin-4-yl)propionamide (1 equiv., $6.40 \times 10^{-4}$ mol), 0.145 g of 2-(thiophen-2-yl)ethyl methanesulfonate (1.1 equiv., $7.04 \times 10^{-4}$ moles), 0.097 g of $K_2CO_3$ (1.1 equiv., $7.04 \times 10^{-4}$ mol), 0.032 g of KI ($1.92 \times 10^{-4}$ mol), and 0.178 mL of $Et_3N$ (2 equiv., $1.28 \times 10^{-3}$ mol) were added to a round bottom flask and dissolved in 5 mL of dry acetonitrile. The reaction mixture was stirred and refluxed overnight. The solvent was then removed via rotary evaporation followed by the addition of $H_2O$. The mixture was extracted with ethyl acetate (3×5 mL), and the organic extracts were combined and dried over anhydrous magnesium sulfate. The solvent was removed via rotary evaporation. The crude product was washed with hexanes to obtain an analytically pure sample. Yield: 0.101 g (60%).

Synthesis of 1-phenethylpiperidin-4-one oxime 28.35 g (1 equivalent, 0.14 mol) of 1-benzylpiperidin-4-one were dissolved in 60 mL of EtOH and then cooled to 0° C. using an ice bath. A solution containing 19.46 g (2 equivalents, 0.28 mol) of hydroxylamine hydrochloride dissolved in 75 mL of $H_2O$ was prepared and then added dropwise to the reaction mixture followed by dropwise addition of a solution containing 19.35 g (1 equivalent, 0.14 mol) of $K_2CO_3$ dissolved in 75 mL of $H_2O$. The reaction mixture was then brought to room temperature and stirred overnight. The EtOH was then removed via rotary evaporation and the reaction mixture was then cooled in an ice bath to allow the product to crystallize out of solution. The product was filtered and washed several times with $H_2O$ and recrystallized in EtOH. Yield: 25.60 g (83.77%).

Synthesis of 1-phenethylpiperidin-4-amine

A solution containing 6.00 g (1 equiv., 0.027 mol) of 1-phenethylpiperidin-4-one oxime dissolved in 90 mL of iso-amyl alcohol was prepared and heated to approximately 110° C. 6.21 g (10 equiv., 0.27 mol) of Na metal was then added slowly to the reaction mixture. After addition of Na, the reaction mixture was allowed to cool to room temperature and stirred until the reaction mixture turned into a thick slurry. The slurry was dissolved in 50 mL of ethyl acetate and 25 mL of $H_2O$. The organic layer was separated and washed with $H_2O$ (2×20 mL) followed by drying over anhydrous magnesium sulfate. The solvent was removed via rotary evaporation, resulting in a yellow oil. The crude product was purified via column chromatography utilizing silica gel and a DCM:MeOH solvent system in a ratio of 4:1 containing an additional 1% of $Et_3N$.

Synthesis of N-(1-phenethylpiperidin-4-yl)furan-2-carboxamide (CRA8)

A solution of 0.1 g of 1-phenethylpiperidin-4-amine (1 equiv., $4.89 \times 10^{-4}$ mol) dissolved in 2 mL of dry dichloromethane was prepared followed by the addition of 0.178 mL (2.6 equiv., $1.27 \times 10^{-3}$ moles) of $Et_3N$. The reaction mixture was then cooled to 0° C. using an ice bath, and then 0.063 mL (1.3 equiv., $6.36 \times 10^{-4}$ mol) of 2-furoyl chloride dissolved in 0.25 mL of dry dichloromethane was added dropwise to the reaction mixture. The reaction mixture was then warmed to room temperature and stirred overnight. Once the reaction was complete, 4 mL of $NH_4OH$ and 45 mL of $H_2O$ were added to the reaction mixture. The organic layer was separated, and the aqueous layer was washed with dichloromethane (3×5 mL) followed by $NaHCO_3$ solution and brine. The organic extracts were dried over anhydrous magnesium sulfate and the solvent was removed via rotary evaporation, resulting in a white solid. The product was washed with hexanes to obtain an analytically pure sample. Yield: 0.0845 g (58.3%).

Synthesis of N-(1-phenethylpiperidin-4-yl)furan-3-carboxamide (CRA9)

A solution of 0.1 g of 1-phenethylpiperidin-4-amine (1 equiv., $4.89 \times 10^{-4}$ mol) dissolved in 2 mL of dry dichloromethane was prepared followed by the addition of 0.178 mL (2.6 equiv., $1.27 \times 10^{-3}$ mol) of $Et_3N$. The reaction mixture was then cooled to 0° C. using an ice bath, and then 0.063 mL (1.3 equiv., $6.36 \times 10^{-4}$ mol) of 3-furoyl chloride dissolved in 0.25 mL of dry dichloromethane was added dropwise to the reaction mixture. The reaction mixture was then warmed to room temperature and stirred overnight. Once the reaction was complete, 4 mL of $NH_4OH$ and 45 mL of $H_2O$ were added to the reaction mixture. The organic layer was separated, and the aqueous layer was washed with dichloromethane (3×5 mL) followed by $NaHCO_3$ solution and brine. The organic extracts were dried over anhydrous magnesium sulfate and the solvent was removed via rotary evaporation, resulting in a white solid. The product was washed with hexanes to obtain an analytically pure sample. Yield: 0.104 g (72%).

Synthesis of 8-bromo-N-(1-phenethylpiperidin-4-yl)octanamide (CRA10)

A solution of 0.101 g of 1-phenethylpiperidin-4-amine (1.1 equiv., $4.93 \times 10^{-4}$ mol), 0.1 g of 8-bromooctanoic acid (1.0 equiv., $4.48 \times 10^{-4}$ mol), 0.170 g of HATU (1.0 equiv., $4.48 \times 10^{-4}$ mol), 0.061 g of HOAt (1.0 equiv., $4.48 \times 10^{-4}$ mol), and 0.314 mL of DIEPA (4.0 equiv., 0.0018 mol) in dry DMF was prepared. The reaction mixture was stirred at room temperature overnight. The reaction mixture was then quenched with 0.5 M $KHSO_4$ solution followed by the addition of dichloromethane. The organic and aqueous layers were separated, and the aqueous layer was extracted with dichloromethane (3×5 mL) followed by washing with $NaHCO_3$ solution and Brine. The organic extracts were then dried over anhydrous magnesium sulfate.

Synthesis of 2-(thiophen-2-yl)ethyl Methanesulfonate 2.6 mL of 2-(thiophen-2-yl)ethanol (1 equiv., 0.023 mol) was dissolved in 45 mL of dry dichloromethane followed by the addition of 3.63 mL of $Et_3N$ (1.13 equiv., 0.026 mol). The reaction mixture was stirred at room temperature for 1 h. It was then cooled to −5° C. using an ice bath and solid NaCl. Once cooled, 1.92 mL of methanesulfonyl chloride was added dropwise over the course of 10 min. The reaction mixture was then warmed to room temperature and stirred for 1 h. Once the reaction was complete, 30 mL of $NaHCO_3$ solution was added followed by separation of the organic and aqueous layers. The aqueous layer was extracted with dichloromethane (3×30 mL). The combined organic extracts were dried over anhydrous magnesium sulfate and the solvent was removed via rotary evaporation, resulting in a brown oil. No further purification was required.

Synthesis of N-(1-Phenethylpiperidin-4-yl)propionamide

Propionyl chloride 2.775 g (0.03 mol) in 5.55 mL of $CHCl_3$ was added dropwise to a cooled (0° C.) solution of 4.08 g (0.02 mol) 1-phenethylpiperidin-4-amine and 3.03 g (0.03 mol) of $Et_3N$ in 30 mL of $CHCl_3$. The mixture was allowed to reach room temperature and stirred overnight. After work-up with 5% aqueous solution of $NaHCO_3$, organic layer was separated, washed with water, dried over $MgSO_4$, and filtered. Filtrate was concentrated and crystallized from hexane to give 4.9 g (94%) of N-(1-phenethyl-piperidin-4-yl)propionamide. M.p. 134-135° C. MS (ESI): 261.2 (MH+). $^1$H NMR (600 MHz, $CDCl_3$): δ 7.27 (t, J=7.4 Hz, 2H), 7.19 (m, 3H), 5.32 (d, J=7.4 Hz, 1H), 3.82 (qt, J=7.8, 4.2 Hz, 1H), 2.92 (dt, J=11.8, 3.4 Hz, 2H), 2.79 (m*, 2H), 2.59 (m*, 2H), 2.19 (q, J=7.5 Hz, 2H), 2.18 (m, 2H), 1.95 (dtd, J=12.4, 4.4, 1.7 Hz, 2H), 1.46 (qd, J=11.7, 3.8 Hz, 2H), 1.15 (t, J=7.5 Hz, 3H). $^{13}$C NMR (150 MHz, $CDCl_3$): δ 173.0, 140.2, 128.6, 128.4, 126.0, 60.4, 52.3, 46.3, 33.7, 32.3, 29.8, 9.9.

Synthesis of N-(1-Phenethylpiperidin-4-yl)propionamide Oxalate

Oxalic acid 1 g (0.011 mol) in 10 mL of ethanol was added dropwise to the solution of 2.93 g (0.011 mol) of N-(1-phenethylpiperidin-4-yl)propionamide in 29.3 mL of ethanol. The mixture was left overnight. Obtained crystals were separated and dried in dessicator over $P_2O_5$ to give 3.5 g of N-(1-phenethylpiperidin-4-yl)propionamide oxalate. M.P. 216-218° C. MS (ESI): 261.2 (M+). X-ray crystallography data for a representative compound of the invention, N-(1-phenethyl-piperidin-4-yl)propionamide oxalate confirmed the structure.

Synthesis of N-(1-phenethylpiperidin-4-yl)benzamide

A solution of benzoyl chloride 0.89 g, (0.00636 mol) in 0.25 mL of dry dichloromethane was added dropwise to a cooled (0° C.) solution of 1.08 g (0.00468 mol) 1-phenethylpiperidin-4-amine and 0.178 mL of $Et_3N$ in 2 mL of $CHCl_3$. The mixture was allowed to reach room temperature and stirred for a night. After work-up with 5% solution of $NaHCO_3$, organic layer was separated, washed with water, dried over $MgSO_4$, and filtered. Concentration of the filtrate gave a white solid. The product was washed with hexanes to obtain an analytically pure sample. Yield: 0.132 g (87%). MS (ESI): 309.2 (MH+). $^1$H NMR (400 MHz, $CDCl_3$): δ 1.35 (t, J=7.29, 7.29 Hz, 2H), 1.64 (qd, J=3.80, 11.29, 11.29, 11.35 Hz, 2H), 2.08 (m, 2H), 2.27 (td, J=2.57, 11.61, 11.65 Hz, 2H), 2.64 (m, 2H), 2.83 (m, 2H), 3.00 (m, 3H), 4.04 (dddd, J=4.28, 8.29, 10.85, 15.24 Hz, 1H), 6.04 (d, J=7.94 Hz, 1H), 7.25 (m, 5H), 7.44 (m, 3H), 7.75 (m, 2H). $^{13}$C NMR (100 MHz, $CDCl_3$): δ 32.22, 33.71, 45.83, 46.97, 52.38, 60.42, 114.25, 126.12, 126.86, 128.42, 128.56, 128.68, 131.42, 134.75, 140.11, 166.88. Obtained compound was transformed to oxalate salt as described above.

Synthesis of 1-Benzylpiperidin-4-one Oxime

A solution of 1-benzylpiperidin-4-one (28.35 g, 0.15 mol) in 60 mL of EtOH was added to the cooled to 0° C. solution of hydroxylamine hydrochloride (20.85 g, 0.30 mol) in 75 mL of $H_2O$. To the resulting mixture was added a solution of $K_2CO_3$ (20.7 g, 0.15 mol) in 75 mL of $H_2O$. The reaction mixture was then allowed to reach room temperature and stirred overnight. The EtOH was removed and the reaction mixture was cooled in an ice bath to allow the product to crystallize out of solution. The product was filtered and washed several times with $H_2O$ and recrystallized in EtOH. Yield: 27.78 g (70.17%).

Synthesis of 1-Benzylpiperidin-4-amine

Na metal (6.9 g, 0.3 mol) was added to a 110° C. solution of 1-benzylpiperidin-4-one oxime (6.12 g, 0.03 mol) in 90 mL of iso-amyl alcohol. The reaction mixture was allowed to cool to room temperature and stirred until the reaction mixture became a thick slurry. The slurry was dissolved in 50 mL of diethyl ether and 25 mL of $H_2O$. The organic layer was separated, washed with $H_2O$, dried over anhydrous magnesium sulfate, and filtered. The filtrate was concentrated to yield a yellow oil. The crude product was purified via column chromatography using silica gel and a DCM:MeOH solvent in a ratio of 4:1 with an additional 1% of $Et_3N$. Yield: 3.7 g (64%).

Synthesis of N-(1-Benzylpiperidin-4-yl)propionamide

To a 0° C. solution of 1-benzylpiperidin-4-amine (3.7 g, 0.019 mol) and 5 mL of $Et_3N$ (0.05 mol) in 45 mL of dry dichloromethane was added a solution of propionyl chloride (2.17 mL, 0.025 mol) in 10 mL of dichloromethane. The reaction mixture was allowed to reach room temperature and stirred overnight. To the reaction mixture was added 4 mL of $NH_4OH$ and 45 mL of $H_2O$. The aqueous layer was separated and extracted with dichloromethane. The combined organic layers were washed with $NaHCO_3$ solution and brine, dried over anhydrous magnesium sulfate, filtered and concentrated to yield a white solid. The product was washed with hexanes to obtain an analytically pure sample. Yield: 2.8 g (72%)

Synthesis of N-(Piperidin-4-yl)propionamide

A solution of N-(1-benzylpiperidin-4-yl)propionamide (0.7 g, 0.003 mol) in 30 mL of EtOH was hydrogenated for 24 hours under 50 psi of $H_2$ in the presence of 10% Pd/C (0.07 g) and 20% $Pd(OH)_2$ (0.07 g). The solution was filtered through Celite and the solvent was evaporated to yield 0.467 g (99%) of the product.

Synthesis of methyl 3-(4-propionamidopiperidin-1-yl)propanoate

A solution of N-(piperidin-4-yl)propionamide (0.1 g, 0.0052 mol) in 2 mL of dry acetonitrile and methyl acrylate (0.071 mL, 0.00789 mol) was refluxed overnight. The solvent was removed and the crude product was purified by washing with hexanes to yield 0.90 g (71%) of the product. MS (ESI): 243.3 (MH+). $^1$H NMR (400 MHz, $CDCl_3$): δ 1.14 (t, J=7.59, 7.59 Hz, 3H), 1.41 (dtd, J=3.70, 11.10, 11.13, 12.61 Hz, 2H), 1.91 (m, 2H), 2.17 (m, 4H), 2.49 (m, 2H), 2.68 (m, 2H), 2.81 (m, 2H), 3.67 (s, 3H), 3.78 (dddd, J=4.29, 4.36, 11.92, 15.26, 1H), 5.25 (d, J=7.96 Hz, 1H). $^{13}$C NMR (100 MHz, $CDCl_3$): δ 10.02, 29.99, 32.41, 46.40, 51.76, 52.25, 55.63, 173.14, 174.05. Obtained compound was transformed to oxalate salt as described above.

Synthesis of N-(1-(2-(Thiophen-2-yl)ethyl)piperidin-4-yl)propionamide

A solution of N-(piperidin-4-yl)propionamide (0.1 g, 0.0064 mol), 2-(thiophen-2-yl)ethyl methanesulfonate (0.145 g, 0.704 mol), $K_2CO_3$ (0.097 g, 0.00704 mol), KI (0.032 g, 0.00192 mol), $Et_3N$ (0.178 mL, 0.00128 mol) in 5 mL of dry acetonitrile was stirred overnight under refluxing conditions. The mixture was concentrated, and the residue was diluted with $H_2O$ and extracted with ethyl acetate. The organic extracts were combined, dried over anhydrous magnesium sulfate, filtered and concentrated. The crude product was washed with hexanes to obtain an analytically pure sample. Yield: 0.101 g (60%). MS (ESI): 267.7 (MH+). $^1$H NMR (400 MHz, $CDCl_3$) δ 1.15 (t, J=7.58, 7.58 Hz, 3H), 1.47 (m, 2H), 1.95 (m, 2H), 2.18 (m, 4H), 2.64 (dd, J=6.87, 8.62 Hz, 2H), 2.90 (m, 2H), 3.00 (m, 2H), 3.82 (dddd, J=4.20, 8.31, 10.86, 15.17 Hz, 1H), 5.32 (d, J=7.95 Hz, 1H), 6.81 (dq, J=1.02, 1.02, 1.02, 3.20 Hz, 1H), 6.91 (dd, J=3.39, 5.14 Hz, 1H), 7.11 (dd, J=1.21, 5.13 Hz, 1H). $^{13}$C NMR (100 MHz, $CDCl_3$) δ 10.04, 28.06, 30.03, 32.15, 46.52, 52.42, 59.98, 123.62, 124.71, 126.69, 142.87, 173.15. Obtained compound was transformed to oxalate salt as described above.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for treating a clinical condition selected from the group consisting of: hemorrhagic shock, nicotine withdrawal symptoms, gastrointestinal side effects of opioids, epithelial wounds, herpes zoster infection, opioid overdose, opioid dependency, and opioid-induced pruritus, said method comprising administering to a subject in need of such a treatment a therapeutically effective amount of a compound of the formula:

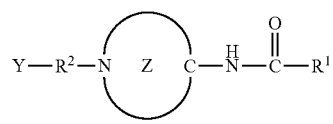

I wherein
ring Z is a 5-, 6- or 7-membered ring;
$R^1$ is $C_{1-10}$ alkyl, $C_{1-10}$ haloalkyl, optionally substituted aralkyl, optionally substituted aryl, optionally substituted heteroaryl or optionally substituted heteroaralkyl;
$R^2$ is $C_{1-10}$ alkylene; and
Y is optionally substituted aryl, optionally substituted heteroaryl, or a moiety of the formula $—C(=O)—X^1$, wherein $X^1$ is $—OR^3$ or $—NR^4R^5$, where each of $R^3$, $R^4$ and $R^5$ is H or $C_{1-10}$ alkyl.

2. The method of claim 1, wherein $R^1$ is selected from the group consisting of ethyl, 7-bromoheptyl, optionally substituted fur-2-yl, optionally substituted fur-3-yl, optionally substituted thiophen-2-yl, optionally substituted thiophen-3-yl, and optionally substituted phenyl.

3. The method of claim 2, wherein $R^1$ is optionally substituted fur-2-yl, optionally substituted fur-3-yl, optionally substituted thiophen-2-yl, optionally substituted thiophen-3-yl or optionally substituted phenyl.

4. The method of claim 1, wherein $R^2$ is $C_1$-$C_4$ alkylene.

5. The method of claim 1, wherein Y is selected from the group consisting of optionally substituted phenyl, optionally substituted thiophen-2-yl, optionally substituted thiophen-3-yl, optionally substituted fur-2-yl, optionally substituted fur-3-yl, a moiety of the formula $—C(=O)—OR^3$, where $R^3$ is $C_1$-$C_{10}$ alkyl, and a moiety of the formula $—C(=O)NR^aR^b$, where each of $R^a$ and $R^b$ is independently H or $C_1$-$C_{10}$ alkyl.

6. The method of 5, wherein Y is optionally substituted phenyl, optionally substituted thiophen-2-yl, optionally substituted thiophen-3-yl, optionally substituted fur-2-yl or optionally substituted fur-3-yl.

7. The method of claim 1, wherein said compound is of the formula:

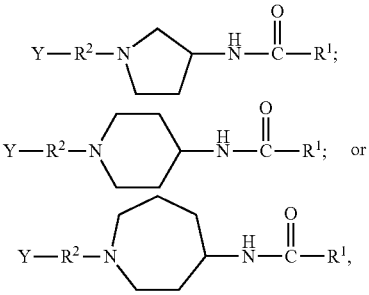

wherein $R^1$, $R^2$ and Y are those defined in claim 1.

8. The method of claim 1, wherein said compound is of the formula:

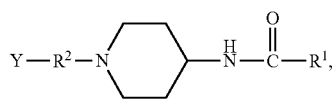

wherein $R^1$, $R^2$ and Y are those defined in claim 1.

9. The method of claim 1, wherein said clinical condition is opioid overdose or opioid dependency.

10. A method for treating a clinical condition selected from the group consisting of: Raynaud's disease, hypertension, scleroderma, anxiety and panic disorder, and dyskinesia associated with Parkinson's disease, said method comprising administering to a subject in need of such a treatment a therapeutically effective amount of a compound of the formula:

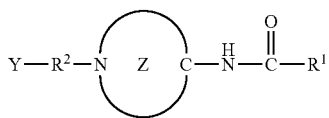

wherein
ring Z is a 5-, 6- or 7-membered ring;
R¹ is $C_{1-10}$ alkyl, $C_{1-10}$ haloalkyl, optionally substituted aralkyl, optionally substituted aryl, optionally substituted heteroaryl or optionally substituted heteroaralkyl;
R² is $C_{1-10}$ alkylene; and
Y is optionally substituted aryl, optionally substituted heteroaryl, or a moiety of the formula —C(=O)—X¹, wherein X₁ is —OR³ or —NR⁴R⁵, where each of R³, R⁴ and R⁵ is H or $C_{1-10}$ alkyl.

11. The method of claim 10, wherein R¹ is selected from the group consisting of ethyl, 7-bromoheptyl, optionally substituted fur-2-yl, optionally substituted fur-3-yl, optionally substituted thiophen-2-yl, optionally substituted thiophen-3-yl, and optionally substituted phenyl.

12. The method of claim 11, wherein R¹ is optionally substituted fur-2-yl, optionally substituted fur-3-yl, optionally substituted thiophen-2-yl, optionally substituted thiophen-3-yl or optionally substituted phenyl.

13. The method of claim 10, wherein R² is $C_1$-$C_4$ alkylene.

14. The method of claim 10, wherein Y is selected from the group consisting of optionally substituted phenyl, optionally substituted thiophen-2-yl, optionally substituted thiophen-3-yl, optionally substituted fur-2-yl, optionally substituted fur-3-yl, a moiety of the formula —C(=O)—OR³, where R³ is $C_1$-$C_{10}$ alkyl, and a moiety of the formula —C(=O)NR$^a$R$^b$, where each of R$^a$ and R$^b$ is independently H or $C_1$-$C_{10}$ alkyl.

15. The method of 14, wherein Y is optionally substituted phenyl, optionally substituted thiophen-2-yl, optionally substituted thiophen-3-yl, optionally substituted fur-2-yl or optionally substituted fur-3-yl.

16. The method of claim 10, wherein said compound is of the formula:

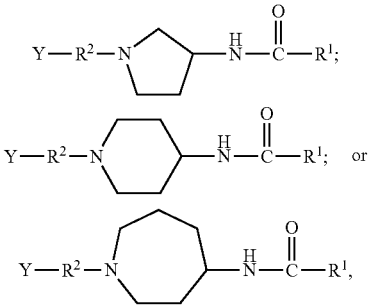

wherein R¹, R² and Y are those defined in claim 10.

17. The method of claim 10, wherein said compound is of the formula:

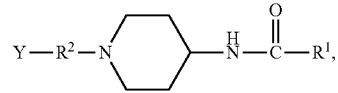

wherein R¹, R² and Y are those defined in claim 10.

* * * * *